Figure 1:
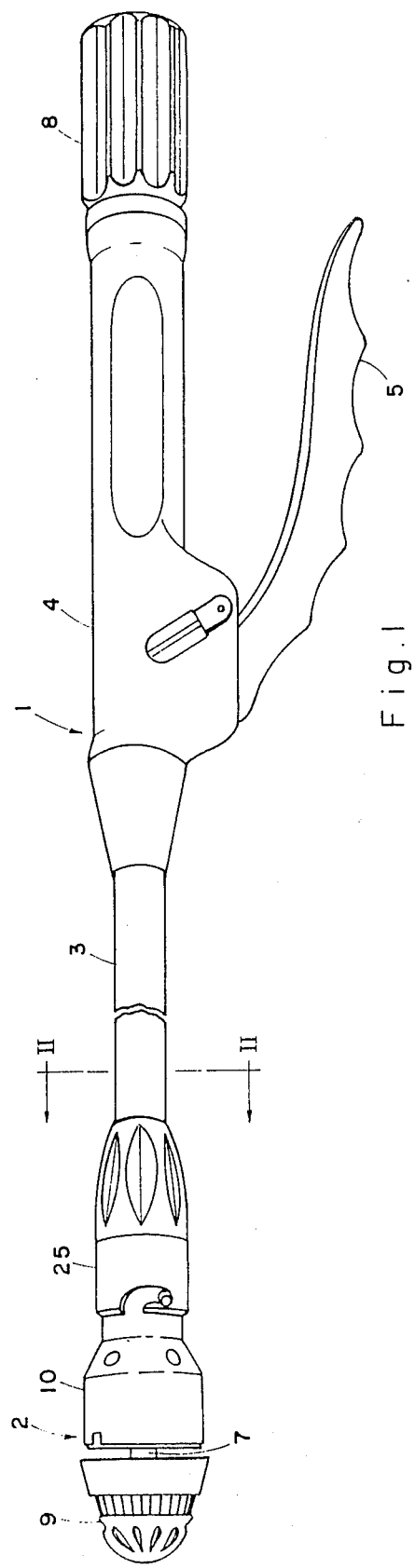

United States Patent [19]

Resnick et al.

[11] Patent Number: 4,903,697
[45] Date of Patent: Feb. 27, 1990

[54] CARTRIDGE ASSEMBLY FOR A SURGICAL STAPLING INSTRUMENT

[75] Inventors: Semion Resnick, 47b Deganiot Street, Kiriat Tivon 36 000; Jacob Goldman, Naharya, both of Israel

[73] Assignee: Semion Resnick, Kiriat Tivon, Israel

[21] Appl. No.: 240,346

[22] Filed: Sep. 1, 1988

Related U.S. Application Data

[63] Continuation of Ser. No. 110,047, Oct. 15, 1987, abandoned, which is a continuation of Ser. No. 844,949, Mar. 27, 1986, Pat. No. 4,700,703.

[51] Int. Cl.[4] ............................................. A61B 17/10
[52] U.S. Cl. .................................... 227/178; 227/19; 227/155; 227/180
[58] Field of Search ............... 128/334 R, 334 C, 305; 227/DIG. 1, 19, 155

[56] References Cited

U.S. PATENT DOCUMENTS 4,289,133  9/1981  Rothfuss .
4,304,236  12/1981  Gonta et al. .
4,505,272  3/1985  Utamyshev et al. ....... 128/334 R X
4,505,414  3/1985  Filipi .......................... 128/334 R X Primary Examiner—Michael H. Thaler
Attorney, Agent, or Firm—Browdy and Neimark

[57] ABSTRACT

A disposable cartridge assembly for a surgical stapling instrument wherein an anvil carrying component comprises constituent anvil elements articulated with respect to each other and presenting an annular anvil surface. A biasing element is provided for biassing the elements into a retracted position wherein the anvil surface has a first diameter. A locking element is provided for releasable interengagement with the anvil elements so as to maintain them in an expanded position against the biassing force wherein the anvil surface has a second larger diameter and so as to lock said elements against relative displacement, the arrangement being such that upon disengagement of the locking element from the anvil elements, the latter are displaced under the biassing force into the retracted position.

4 Claims, 8 Drawing Sheets

CARTRIDGE ASSEMBLY FOR A SURGICAL STAPLING INSTRUMENT

This is a continuation of co-pending parent application Ser. No. 110,047, filed Oct. 15, 1987, abandoned, itself a continuation of application Ser. No. 844,949, filed Mar. 27, 1986, now U.S. Pat. No. 4,700,703.

This invention relates to an improved cartridge assembly for a surgical stapling instrument and is particular directed to a surgical stapling instrument for joining together, by stapling, the cut ends of tubular body organs.

Such surgical stapling instruments have been known for some time and are now in widespread use. Examples thereof are described in the prior art such as, for example, U.S. patent Ser. Nos. 4,289,133 and 4,304,236.

With such known surgical staping instruments of the kind to which the present invention is particularly directed, the instrument is adapted to be fitted with a disposable cartridge assembly. This assembly is of a kind comprising a staple and anvil carrying components. The stape carrying component has one or more annular arrays of staples surrounding a cylindrical scalpel having a cylindrical scalpel knife edge disposed adjacent to and inwardly of the staples, these being furthermore provided with staple and scalpel drivers. The anvil bearing component has an anvil surface formed with one or more annular arrays of staple clinching grooves. The componebnts are adapted to be mounted with respect to an elongated tubular housing of the surgical stapling instrument so as to be capable of relative movement towards and away from each other and so that, when the staple bearing component is juxtaposed with respect to the anvil bearing component respectively within a pair of tubular body organs to be joined together by staping and with the cut ends of the tubular body organs interposed between the juxtaposed components, the instrument can be actuated so as to drive the staples through the cut ends so as to effect stapling and so as to drive the scalpel towards the anvil bearing member thereby severing excess tissue.

Such a cartridge assembly will hereinafter be referred to as a cartridge assembly of the kind specified.

Surgical stapling instruments for use with cartridge assemblies of the kind specified comprise an elongated tubular housing, one end of which is formed integrally with an instrument handle and to the other end of which there is releasably coupled the staple carrying component. Extending through the tubular housing is an adjustment rod to one end of which, adjacent the instrument handle, is coupled adjusting means, and to the other end of which, extending out of the tubular housing, is releasably coupled the anvil carrying component. The instrument is furthermore provided with actuatable means such as, for example, a trigger which is articulated to a tubular driver rod or the like, axially displaceable within the housing and which is in turn coupled to the staple and scalpel drivers.

In use with the cartridge assembly components mounted on the instrument with the staple clinching grooves of the anvil carrying component suitably aligned with the staples of the staple carrying component, the operative end of the instrument (the end bearing the cartridge assembly) is inserted into the hollow body organs whose cut ends are to be secured together by stapling. The anvil carrying component is suitably spaced away from the staple carrying component by suitable rotation of the adjustment means so that one component is located in one organ and the other component is located in the other organ and the cut ends of the organs are located between the two components. The anvil carrying component is then displaced towards the staple carrying component, again by suitable turning of the adjustment means until the two components are juxtaposed, with the cut organ ends located therebetween. The instrument trigger (or the like) is then actuated and as a consequence the staples are forced through the cut ends stapling them together and, at the same time the scalpel is forced forward so that the scalpel knife edge cuts away the superfluous tissue.

It will readily be realised that by virtue of this operation there is formed a circular, stapled anastomosis whose inner diameter corresponds to the diameter of the knife edte and the latter, being disposed inwardly of the staple arrays is of necessity substantially less than the diameter of the staple arrays and in consequence, less than the diameter of the anvil surface of the anvil carrying component.

In order to remove the instrument from the narrow stapled together body organ, the anvil carrying component is first of all displaced away from the staple carrying component (and consequently away from the stapled anastomosis) and the tubular housing together with the cartridge assembly components is manipulated out of the tubular organ.

It will be readily seen that, in view of the fast that, as explained above, the external diameter of the anvil carrying component is substantially greater than the internal diameter of the stapled anastomosis, difficulty is encountered in withdrawing the end of the instrument bearing the anvil carrying component through the organ past the anastomosis and this despite the considerable degree of elasticity of the organ tissue.

This difficulty has been recognized in the past and has constituted a limiting factor in the effective use of surgical stapling instruments in effecting circular anastomosis.

One attempt to overcome this difficulty has been described in U.S. Pat. No. 4,289,133 wherein a specific geometrical configuration for the anvil carrying component is prescribed by virtue of which the withdrawal of the anvil bearing component past the circular anastomosis is designed to be rendered easier. It has been found in practice however that, even with this particular geometrical design for the anvil carrying component, considerable difficulties still arise in practice in manipulating the anvil carrying component past the circular anastomosis and these difficulties render the use of the instrument difficult, time consuming and at times even risky.

It is an object of the present invention to provide a new and improved disposable cartridge assembly for a circular staping instrument in which the above-referred to difficulties are significantly reduced.

According to the present invention there is provided, in a disposable cartridge assembly of the kind specified comprising, an anvil carrying component comprising constituent anvil elements articulated with respect to each other and presenting an annular anvil surface, biasing means for exerting a biasing force so as to bias said elements into a retracted position wherein said anvil surface has a first diameter, and a locking element for releasable interengagement with said anvil elements so as to maintain them in an expanded position against the biasing force wherein said anvil surface has a second and larger diameter and so as to lock said elements against relative displacement, the arrangement being such that upon disengagement of the locking element from the anvil elements the latter are displaced under said biasing force into said retracted position.

Thus, with a disposable cartridge assembly of the kind specified, having an anvil carrying component in accordance with the present invention, stapling is effected with the constituent anvil elements maintained in their expanded position and, after stapling has been completed, the biasing means forces the elements into their retracted position wherein the diameter of the anvil surface is now sufficiently reduced so as to allow for the ready removal of the anvil carrying component past the circular anastomosis.

Preferably, the anvil elements are constituted by respective anvil segments, each segment being integrally secured at one end thereof to a central hub portion by a relatively flexible linkage and being formed, at an opposite end thereof, with a component anvil surface, whereby said segments can be flexibly displaced from said retracted to said expanded position. Each anvil segment can be formed, adjacent its opposite end, with a slot which slots together form a groove. The locking element, being constituted by a ring, is adapted to fit into the groove so as to maintain the segments in their expanded position, the ring being furthermore provided with a succession of tooth-like projections adapted to project into the spaces between the segments, thereby preventing movement of the segments with respect to each other.

Thus with the locking ring in position, the segments are forced outwardly into their expanded position against the biasing force exerted by the biasing means, preferably constituted by a compression band formed of silicon rubber or the like and at the same time the individual segments are prevented from movement with respect to each other. In this way the segments constitute an effectively rigid structure with a rigid anvil surface on which is formed the appropriate staple clinching groove. Once the ring is removed, after stapling has taken place, the segments are forced inwardly under the influence of the compression band, thereby reducing the overall diameter of the component sufficiently to allow for its easy withdrawal past the circular anastomosis.

The disengagement of the locking ring with respect to the anvil component is preferably effected by virtue of it having been penetrated by the scalpel knife edge to which it becomes frictionally retained, the ring becoming separated from the anvil component when the latter is moved away from the staple carrying component after stapling has been effected.

Preferably the anvil carrying component further comprises a bored anvil base member to which the instrument adjusting rod is adapted to be coupled, the base member being articulated to the anvil hub portion so as to permit for relative rotational displacement between them.

Figure 2:
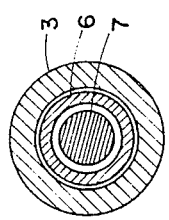
Figure 3:
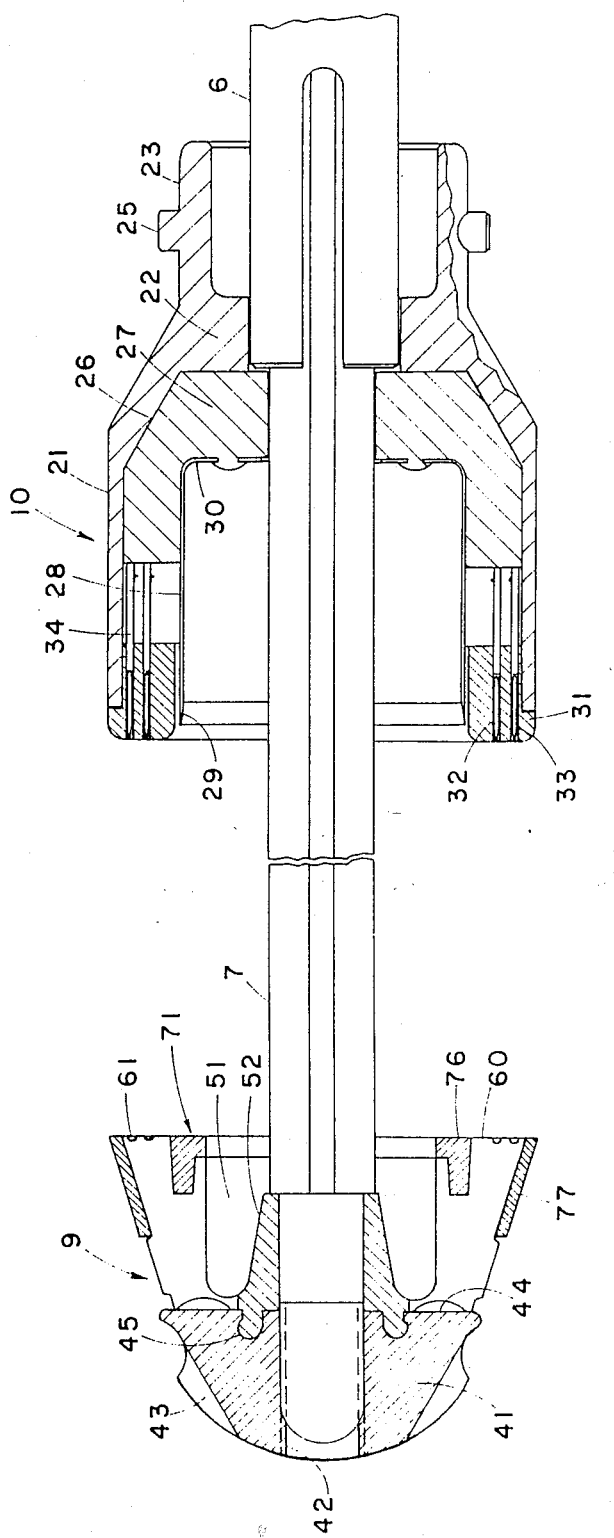
Figure 4:
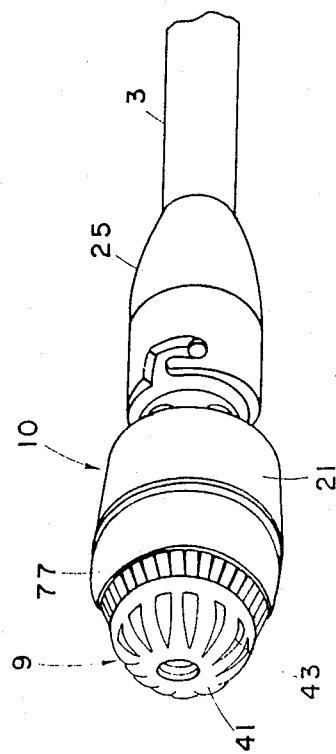
Figure 6:
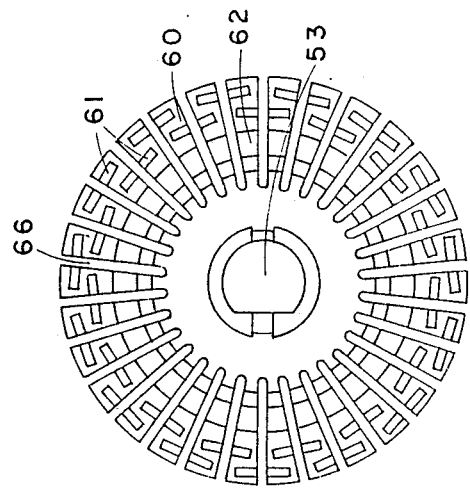
Figure 5:
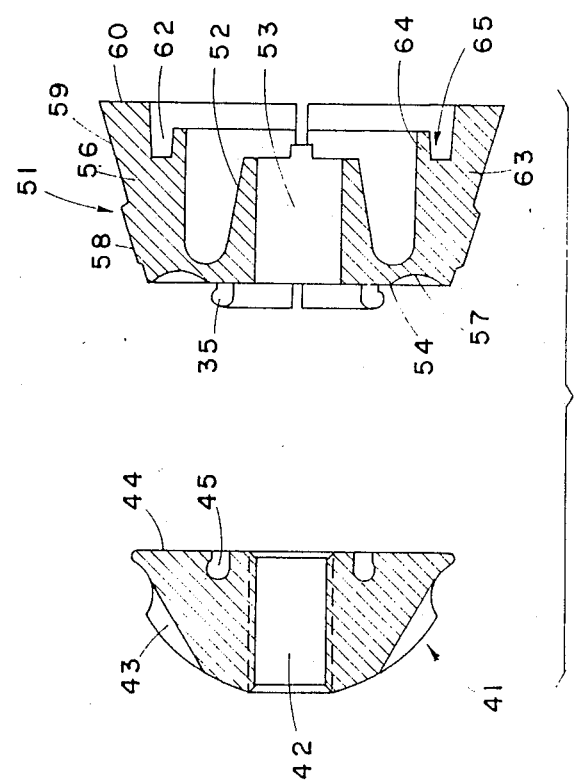
Figure 7:
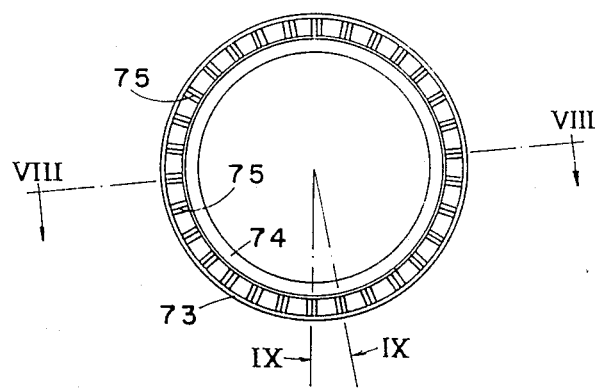
Figure 8:
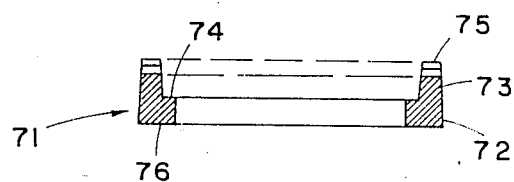
Figure 9:
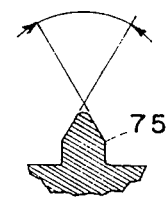
Figure 10:
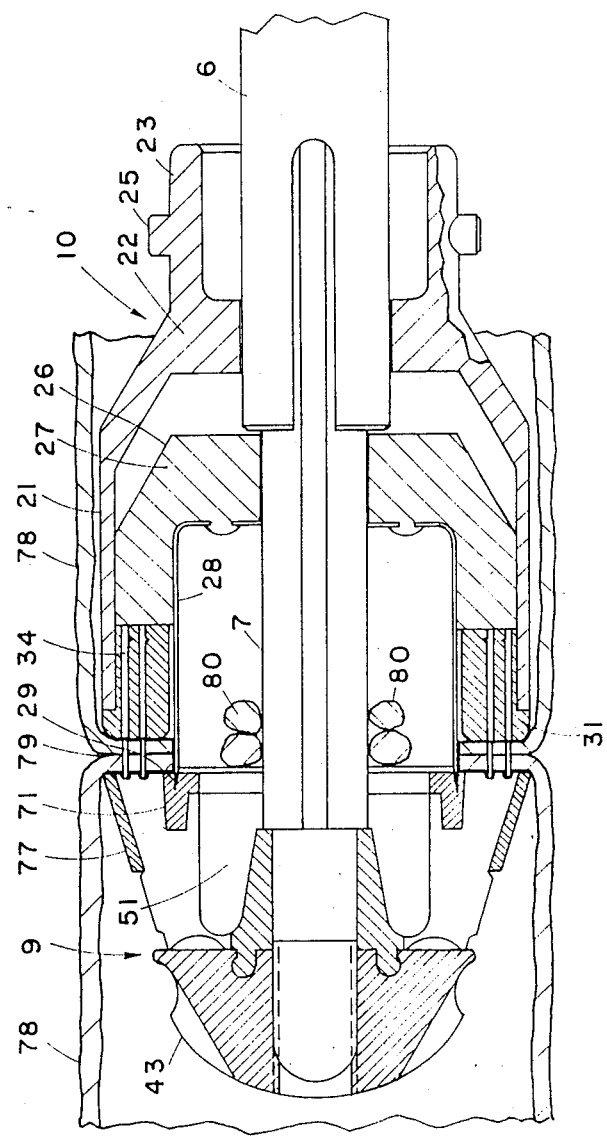
Figure 11:
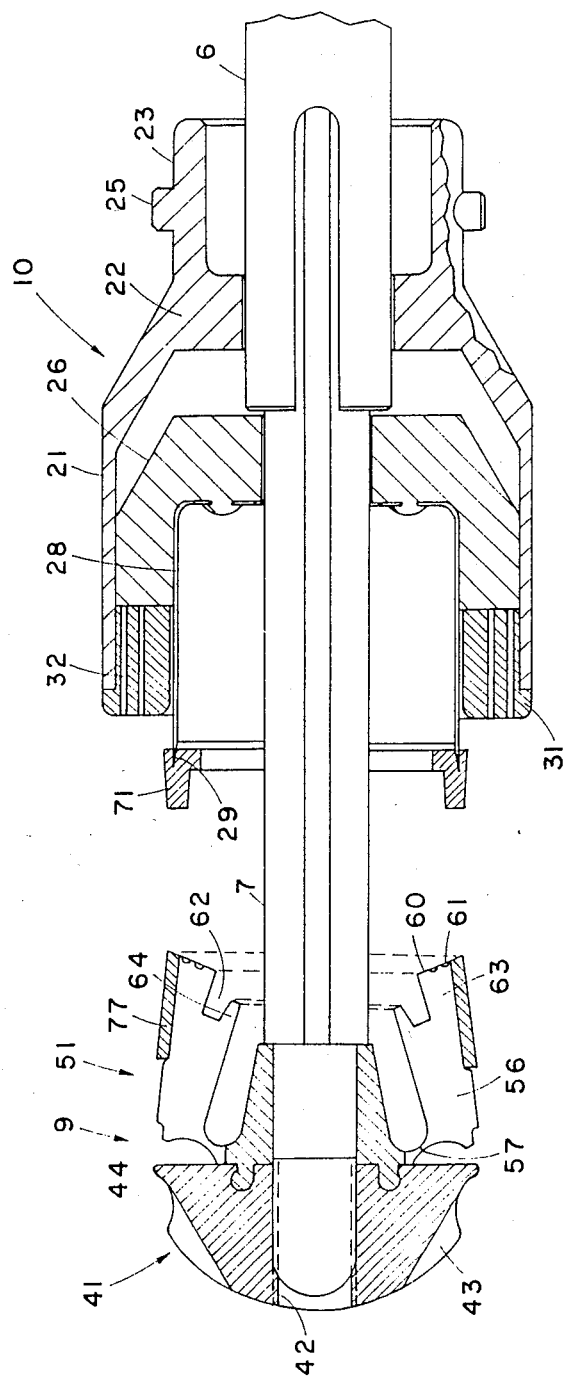
Figure 12:
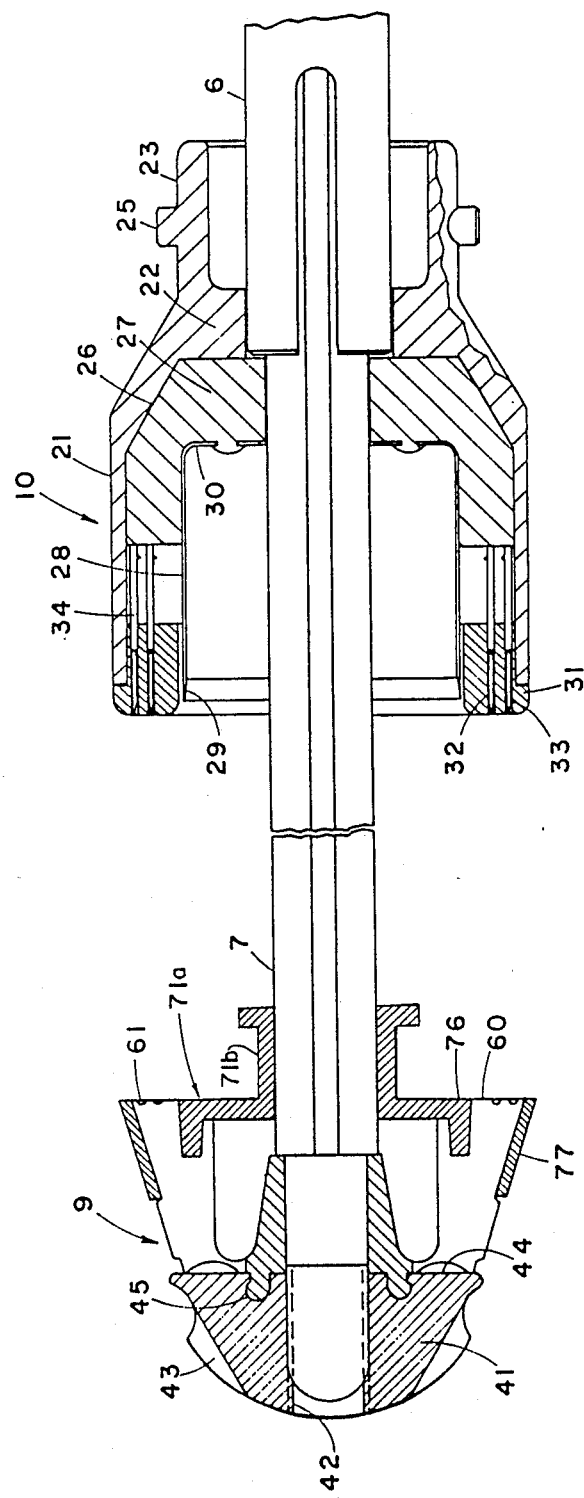

One embodiment of a disposable cartridge assembly in accordance with the present invention for use with surgical stapling apparatus will now be described by way of example and with reference to the accompanying drawings in which:

FIG. 1 is a schematic side elevation of a standard, commercially available surgical stapling instrument to which there is fitted an embodiment of the novel disposable cartridge in accordance with the present invention, FIG. 2 is a cross-sectional view of the surgical stapling instrument shown in FIG. 1 taken along the line II—II, FIG. 3 is a longitudinally sectioned elevation of the disposabled cartridge in accordance with the present invention shown mounted on the surgical stapling instrument with the two constituent elements of the cartridge separated, FIG. 4 is a perspective view of the cartridge shown in FIG. 3 when mounted, FIG. 5 is an exploded, longitudinally sectioned view of one of the elements of the cartridge shown in FIG. 3 constituting an anvil carrying component, FIG. 6 is a plan view, from below of the anvil carrying component of one of the elements of the cartridge shown in FIG. 3 constituting an anvil carrying component, FIG. 7 is a plan view from below of a locking ring constituting an element of the anvil carrying component shown in FIG. 3, FIG. 8 is a cross-sectional view of the ring shown in FIG. 7 taken along the line VIII—VIII, FIG. 9 is a cross-sectional view of the ring shown in FIG. 7 taken along the line IX—IX, FIGS. 10 and 11 are respective longitudinally sectioned views of the disposable cartridge assembly in accordance with the invention mounted on the surgical stapling instrument in two differing stages of operation, namely, during and after completion of anastomosis and prior to removal of the instrument from joined tubular body parts, FIG. 12 is a view of a disposable cartridge corresponding to the view shown in FIG. 3 and showing a modification thereof in accordance with the invention.

Reference will now be made to FIGS. 1 and 2 of the drawings which depict schematically a surgical stapling instrument 1 on which is mounted a disposable cartridge assembly 2 in accordance with the present invention. In view of the fact that the present invention does not relate to the details of construction and operation of the surgical stapling instrument per se, the latter will not be described in any detail.

As seen in FIGS. 1 and 2 the instrument comprises an outer tubular housing 3 which is integrally formed with a fixed rear handle 4 having pivoted thereto a lever 5. As can be seen from FIG. 2 of the drawings, the tubular housing 3 encloses an elongated tubular driver 6 which, in its turn encloses an elongated adjusting rod 7. The rod 7 is formed along its axial extent with a flattened portion (not shown) allowing for the keying of the rod 7 to the cartridge components. One end of the rod 7 is screw coupled to an adjustment nut 8. The opposite end of the rod 7 extends out of the housing 3 and is screw-coupled to an anvil carrying component 9 of the disposable cartridge assembly 1. A staple carrying component 10 of the disposable cartridge assembly 1 is releasably mounted on the tubular housing 3. The actual mode of mounting of the constituent components of the disposable cartridge assembly on the instrument will be described in detail below.

Reference will now be made to FIGS. 3 through 9 of the drawings for a detailed description of the disposable cartridge assembly in accordance with the present invention.

As indicated above, the assembly 1 comprises an anvil carrying component 9 and a staple carrying component 10 and particular reference will now be directed to the construction and mode of operation of the anvil carrying component 9 wherein the essential novel aspects of the present invention resides. For the sake of completeness, however, there will now be described the schematically shown staple carrying component 10.

As can be seen in FIG. 3 of the drawings, the staple carrying component 10 comprises an outer housing 21 having a centrally apertured base portion 22 into which is adapted to extend the terminal portion of the tubular driver 6 and from which extends a coupling collar 23 having coupling pins 24 by means of which the component is bayonet coupled within a receiving cup 25 formed integrally with the end of the external tubular housing 3 (see FIGS. 1 and 4). Located within the housing 21 is a pusher member 26 having a centrally apertured base 27 through which extends the adjusting rod 7 and which is abutted by the end of the tubular driver 6. A cylindrical scalpel 28 is formed at one end with a knife edge 29 and at its opposite edge with an inwardly flanged, centrally apertured, support base 30 which is secured to the base 27 of the pusher member 26. Fitted to the mouth of the outer housing 21 is an annular staple guide member 31 in which are formed two concentric, spaced staple receiving slots 32 containing two circular sets of staples 33. Located between the inner edges of the staples 33 and the pusher member 26 is a pair of concentric cylindrical pusher plates 34.

Means (not shown) are provided for ensuring that the staple carrying component 10 is mounted with respect to the outer tubular housing 3 in an accurately predetermined angular disposition.

The anvil carrying component 9 comprises a knob shaped base member 41 having a central, tapped throughgoing bore 42 and having an external fluted surface 43 and a planar base surface 44 in which is formed a circular groove 45, concentric with the thoroughgoing bore 42.

A segmented anvil member 51 comprises a central hub 52 having a thoroughgoing axial bore 53, this bore 53 being keyed so as to be capable of receiving in a non-rotatable fashion, the correspondingly keyed adjusting rod 7. Thus, similarly to the staple carrying component 10, the anvil carrying component 9 is mounted in a precise, accurately predetermined angular disposition. The outer surface of the hub 52 is conically tapered. The upper end of the hub 52 is formed integrally with an annular planar surface 54 and with projecting beaded rib 35 adapted to be snap fitted within the circular groove 45 of the base member. Thus the anvil member 51 is rotatable with respect to the base member 41.

Formed integrally with, and extending radially out of the hub 52, are a plurality of radially directed anvil segments 56, each segment being linked to the hub via a narrow flexible neck 57. Each segment 56 extends in a substantially axial direction, the outer edge 58 of each segment 56 being formed with a recessed portion 59, the outer edges 58 of the segments 56 as a whole defining a substantially conical, tapering surface with a peripheral recess.

An edge 60 of each segment 56 remote from the neck 57 constitutes a component anvil surface, the edges 60 of all the segments defining an annular anvil surface in which are formed a pair of concentric, staple clinching grooves 61.

Each segment 56 is formed, adjacent the edge 60 thereof with a slot 62 located between a segment leg 63 and a segment projection 64 which is inset with respect to the segment edge 60.

These slots 61 in the segments 56 define a groove 65 between the outer segment legs 63 and the inner segment projections 64. The successive segments 56 are separated from each other by a spacing 66.

Referring to FIGS. 7, 8 and 9, a spacing and locking ring 71 comprises an annular base portion 72 formed integrally with a tapered portion 73, the two portions merging with each other via a stepped shoulder 74. The tapered portion 73 is surmounted by and formed integrally with a set of projecting tapering teeth 75. The dimensioning of the ring 71 is such that it can be inserted into the groove 65 formed in the segment 56 so that its tapered portion 73 fits snugly within this groove 65 whilst its stepped shoulder 74 bears against an annular surface presented by the edges of the projections 64 of the segments 56. At the same time, the teeth 75 are respectively located within the spacings 66 between the successive segments 56. When the locking ring is thus seated, as shown in FIG. 3 of the drawings, an exposed annular surface 76 thereof is essentially flush with the anvil surface formed by the coplanar segment edges 60. The location of the ring 71 within the groove 65 and the teeth 75 within the spacings 66 locks the individual segments 56 against inward flexing displacement about their flexible necks 57 and also locks the individual segments 56 against relative movement towards or away from each other.

An elastic compression band 77 is fitted around the lower axial portion of anvil member 51, the band being located within the peripheral recess formed by the recess 59. This compression band 77 tends to bias the individual segments 56 inwardly but this biasing force is resisted and the inward movement of the segments 56 is prevented by the provision of the locking ring 71 as explained above.

As can be seen in FIG. 3 of the drawings, the assembled anvil carrying component 9 is fitted onto the distal end of the adjustment rod 7, the threaded end of this rod being screw fitted into the tapped bore 42 of the base member 41.

With the cartridge assembly 2 fitted onto the surgical stapling instrument 1 and with the constituent components 9 and 10 of the assembly 2 appropriately aligned so that the staples 33 of the staple carrying component 10 are disposed opposite the appropriate staple clinching grooves 61 of the anvil carrying component 10, the instrument 10 can be used in the conventional manner for effecting circular anastomoses and the procedure will not here be described in any detail. Suffice it to say that with the instrument 1 inserted into the hollow tubular body parts whose cut ends are to be stapled together and with the two cut ends of the hollow organ interposed between the anvil carrying component 9 and the staple carrying component 10, the adjustment nut 8 is rotated so as to bring the anvil carrying component 9 into close proximity with the staple carrying component 10. When the two components are suitably positioned for stapling to take place, the staples 33 are pushed forward by suitable actuation of the pivoted lever 5 so as to effect stapling and, at the same time the scalpel 28 is pushed forward so that its knife edge cuts away the superfluous tissue.

As can be seen from FIG. 10 of the drawings, stapling of the cut ends of a pair of hollow tubular body parts 78 and the cutting away, by the knife edge 29 of excess tissue 80 is accompanied by the penetration by the knife edge 29 of the scalpel 28 into the locking ring 71.

Now, when it is desired to remove the instrument 1 after stapling has been completed, the adjustment nut 8 is now rotated in an opposite direction as a result of which the anvil carrying component 9 is displaced inwardly into a position as shown in FIG. 11 of the drawings. In view of the fact however that the knife edge 29 of the scalpel 28 has penetrated the locking ring 71, the latter remains fixedly attached to the scalpel 28 and with the outward movement of the anvil carrying component 9 the locking ring 71 becomes detached from the anvil carrying component 9 and the compressive force exerted by the compression band 77 results in the inward pivotal displacement of the segments 56 with the consequent overall substantial reduction in the maximum diameter of the anvil carrying component 9 to a diameter less than that of the knife edge 29. With this reduction in diameter the anvil bearing component can readily pass through the stapled anastomosis 79 seeing that its overall diameter is now less than that of the stapled anastomosis 79.

Upon removal of the instrument from the body the two components of the cartridge assembly can be readily removed and disposed of.

It will be readily appreciated that, by virtue of the provisions of an anvil carrying component 9 which, in its prestapling condition, presents an annular surface of a required predetermined diameter whilst in its post-stapling condition presents an overall diameter which is less than the diameter of the stapled anastomosis, the use of the instrument is very considerably simplified.

Preferably, the anvil carrying component is formed of a moulded plastic material such as, for example, polypropylene oxide which is provided with a hard chrome coating. The locking ring 71 is formed of a plastic material having the desired characteristics, namely that it serves as a suitabled surface against which the excess tissue can be cut away, allows for the ready insertion of the knife edge and, on the other hand is capable of effectively gripping the inserted knife edge so as to prevent its ready withdrawal therefrom. A suitable material for the locking ring is, for example, high density polyethylene. A suitable material for the compression band is, for example, silicone rubber.

In order to ensure a maximum degree of contraction of the anvil member 51 after removal of the compression band 77, the former should, as in the example described above, be divided into a maximum number of segments. It will be appreciated, however, that where a lesser degree of contraction can suffice the anvil member can be divided into a lesser number of constituent segments.

In accordance with a further modification as shown in FIG. 3, the locking ring 71a is formed integrally with a cylindrical bushing 71b which surrounds the adjusting rod 7 and which extends a short distance towards the cartridge 10 so that when the anvil 9 and the cartridge 10 are brought together the bushing 71b extends into the inner hollow space of the cartridge 10. The end surface of the bushing closest to the cartridge 10 is therefore effective in displacing all superfluous tissue together with any which have undergone "purse string" procedure (including the staping type) into the hollow space prior to the cutting away of the surrounding area by the scalpel.

What we claim is:

1. A disposable cartridge assembly for a surgical stapling instrument and comprising:

a staple carrying component mounted on an elongated tubular element and having one or more annular arrays of staples surrounding a cylindrical scalpel and having a cylindrical scalpel knife edge disposed adjacent to and inwardly of the staples, said staple carrying component being furthermore provided with a staple and scalpel driver;

an anvil carrying component mounted on said elongated tubular element so as to be capable of relative movement towards and away from the staple carrying component and having an annular anvil surface formed with one or more annular arrays of staple clinching grooves and including an annular element located inwardly of said clinching grooves and penetrable by said scalpel knife edge;

a cylindrical bushing formed integrally with said annular element surrounding said elongated tubular element and extending therefrom in the direction of said staple carrying component so that when the components are brought together, the bushing extends into a narrow hollow space of the staple carrying component;

said anvil carrying component furthermore comprising constituent anvil elements articulated with respect to each other and presenting said annular anvil surface, each segment being integrally secured at one end thereof to a central hub portion by a relatively flexible linkage and being formed at an opposite end thereof with a component anvil surface, said component anvil surfaces together forming said annular anvil surface;

biasing means for biasing said elements into a retracted position wherein said annular anvil surface has a first diameter;

a locking element for releasable interengagement with said anvil elements so as to maintain them in an expanded position against a biasing force exerted by said biasing means wherein said anvil surface has a second larger diameter and so as to lock said elements against relative displacement so that upon disengagement of said locking element from said anvil elements, the latter are displaced under said biasing force into said retracted position;

each anvil segment being formed adjacent said opposite end with a slot which together form a groove, said locking element being constituted by said annular element adapted to fit into said groove so as to maintain said segments in their expanded position, said annular element being furthermore formed with a succession of tooth like projections adapted to project into the spaces between the segments thereby to prevent movement of the segments with respect to each other.

2. The improvement according to claim 1 wherein said biasing means is constituted by a compression band which is tightly fitted around said segments.

3. The improvement according to claim 2 and furthermore comprising a bored anvil base member to which said elongated tubular element is adapted to be coupled, said base member being articulated to said anvil hub portion so as to permit for relative rotational displacement between them.

4. An anvil carrying component according to claim 3 wherein said hub portion is formed with a circular bead which is adapted to be snap-fitted into a corresponding groove formed in an adjacent surface in said base member so as to allow for said relative rotational displacement.

* * * * *